(12) United States Patent
Hotta

(10) Patent No.: US 7,258,545 B2
(45) Date of Patent: Aug. 21, 2007

(54) ORTHODONTIC ANCHOR

(76) Inventor: Yasunori Hotta, 15-20, 2-chome, Obatanaka, Moriyama-ku, Nagoya-shi, Aichi-ken, 463-0013 (JP)

( * ) Notice: Subject to any disclaimer, the term of this patent is extended or adjusted under 35 U.S.C. 154(b) by 181 days.

(21) Appl. No.: 11/021,818

(22) Filed: Dec. 24, 2004

(65) Prior Publication Data

US 2005/0142513 A1    Jun. 30, 2005

(30) Foreign Application Priority Data

Dec. 26, 2003    (JP)    ............................ 2003-433639

(51) Int. Cl.
*A61C 3/00*    (2006.01)
*A61C 8/00*    (2006.01)

(52) U.S. Cl. .................. 433/18; 433/173; 433/176

(58) Field of Classification Search ................ 433/18, 433/173–174, 176; 606/69, 75–76, 105; 623/17.17, 17.18, 17.19
See application file for complete search history.

(56) References Cited

U.S. PATENT DOCUMENTS

| | | | | |
|---|---|---|---|---|
| 5,052,930 A | * | 10/1991 | Lodde et al. | ................ 433/173 |
| 5,513,989 A | * | 5/1996 | Crisio | ......................... 433/176 |
| 5,538,427 A | * | 7/1996 | Hoffman et al. | ............. 433/173 |
| 5,853,291 A | * | 12/1998 | DeVincenzo et al. | ........ 433/176 |
| 6,827,574 B2 | * | 12/2004 | Payton | ........................... 433/8 |
| 6,896,514 B2 | * | 5/2005 | DeVincenzo | .................. 433/24 |
| 2001/0005575 A1 | * | 6/2001 | Kanomi et al. | ................ 433/18 |
| 2003/0104335 A1 | * | 6/2003 | Chung | ........................... 433/18 |

FOREIGN PATENT DOCUMENTS

| | | | |
|---|---|---|---|
| DE | 3736977 A1 | * | 7/1988 |
| DE | 4036753 A1 | * | 5/1992 |
| JP | 2001-187071 | | 7/2001 |

OTHER PUBLICATIONS

Suzuki Junji; Chiyoda Shobo, "Implant Orthodontics/Dental Laser," *Implants/Laser*, Jul. 27, 2002.
WehrBein, Heinrich, et. al., Bone-to-implant contact of orthodontic implants in humans subjected to horizontal loading, *Clin Oral Impl Res* 9: 348-353, (1998).

* cited by examiner

*Primary Examiner*—John J Wilson
(74) *Attorney, Agent, or Firm*—Arendt & Associates Intellectual Property Group; Jacqueline Arendt

(57) ABSTRACT

An orthodontic anchor is disclosed. The orthodontic anchor has an anchor plate to be embedded between the mandible or maxilla bone and the covering mucous membrane and an engagement plate that remains exposed in the oral cavity. The anchor plate includes a protrusion and tissue openings. The protrusion is to be integrated with a bore prepared in the mandible or maxilla bone and the tissue openings are to be filled in with tissues to provide anchorage. The engagement plate includes engagement openings which are used to engage with a ligament device for correction of malocclusion.

8 Claims, 7 Drawing Sheets

ORTHODONTIC ANCHOR

FIELD OF THE INVENTION

This invention relates to an orthodontic anchor that can be used for correcting of malocclusions.

BACKGROUND TECHNOLOGY

There exists a variety of orthodontic therapies and devices for rectifying of malocclusions. Generally, such therapies require the use of teeth biasing means and anchoring means.

Conventionally, such anchorage may be provided either internally or externally. When provided within the mouth, the anchorage is typically provided by utilizing the molar teeth or using bone implants. "Implant Orthodontics/Dental Laser" (SUZUKI, Junji; CHIYODA SHOBO; 27 Jul. 2002) teaches the use of implants that are partially embedded in the mandible or maxilla bone to provide anchorage for an orthodontic device. JP Patent Application Laid-Open Publication No. 2001-187071 teaches use of an orthodontic device having a base and an extension. The base is screwed to the mandible or maxilla bone to provide the required anchorage.

Conventionally, when a bone implant having a screw-like, stick-like or plate-like base having and an extension is used, the base is directly implanted into the mandible or maxilla bone to provide anchorage for the wiring that is to be connected to the extension. Generally, the implant is painful to patients not only during the implanting processes but also after the implanting processes as well as during the implant removal processes. In addition, the implantation and removal of the implant damages the mandible or maxilla bone and neighboring mucous membranes. Conventional implants also cause feelings of physical disorder or foreign sensation in wearers.

Alternatively a bone jointing plate (miniplate) as used by plastic surgeons may be used as an anchorage means. However, the screw holes of the miniplate are interconnected, and no means are provided to specifically connect any wiring to the plate; thus, such a plastic surgery device is not suitable for use in orthodontic applications.

An orthodontic implant may conventionally be secured to the mandible or maxilla bone with a miniature screw or screws, which do not provide sufficient anchorage because the mandible or maxilla bone is not solid enough to maintain the miniature screw or screws for prolonged use. When the anchorage is not sufficient, a gap may form between the hole of the mandible or maxilla bone and the gap that might be created and may lead to an infection.

Accordingly, it is an object of the present invention to provide an orthodontic anchor that is easy to use.

It is another object of the present invention to provide an orthodontic anchor that allows three-dimensional freedom of manipulation.

It is another object of the present invention to provide an orthodontic anchor that provides reliable and long lasting anchorage.

It is still another object of the present invention to provide an orthodontic anchor that is less painful than conventional orthodontic implants or anchor devices currently in use.

It is yet another object of the present invention to provide an orthodontic anchor that causes less damage to the mandible bone, maxilla bone, or mucous tissues than conventional orthodontic implants or anchor devices.

It is another object of the present invention to provide an orthodontic anchor that causes less irritation to patients than conventional orthodontic implants or anchor devices.

It is yet another object of the present invention to provide an orthodontic anchor that is easier to implant and remove than conventional orthodontic implants or anchor devices.

Other objects and how to achieve all objects of the present invention will be apparent from the following description.

SUMMARY OF THE INVENTION

The orthodontic anchor of the present invention is typically comprised of an anchor plate and an engagement plate. The anchor plate is provided with a protrusion generally at the center of the anchor plate. The protrusion is inserted into an anchor bore prepared in the mandible or maxilla bone for eventual integration with the mandible or maxilla bone. The anchor plate is provided typically with a number of tissue openings generally arranged around the protrusion. The engagement plate is typically provided with engagement openings for engagement with the teeth biasing means or a ligament device. The engagement openings may be replaced by hooking means.

The size of the anchor bore can be minimized to avoid damaging the mandible or maxilla bone excessively and can be formed in the mandible or maxilla bone using a boring device. Each tissue opening is eventually filled in with mucous membrane tissues that are in contact with the tissue openings after the orthodontic anchor is embedded to provide additional anchorage. The anchor plate is placed between the mandible or maxilla bone and the covering mucous membrane.

The mucous membrane tissues that eventually fill in the openings can provide as much as two thirds of the entire anchorage. Therefore, the anchorage required of the protrusion and the tiny anchor bore in the mandible or maxilla bone in combination can be as little as one third of the entire anchorage required for effective orthodontic use. The smallness of the anchor bore greatly contributes to conservation of the mandible or maxilla bone without substantive damage thereto.

The orthodontic anchor of the present invention facilitates easy use and provides long lasting reliable anchorage for correction of malocclusion with limited damage to the mandible or maxilla bone and covering mucous membrane tissues.

The orthodontic anchor of the present invention also allows three-dimensional freedom of manipulation.

The orthodontic anchor of the present invention generates in patients only a limited degree of pain during implantation and removal. The orthodontic anchor of the present invention generates only a limited degree of foreign and irritating feelings during the healing process unlike conventional orthodontic devices.

The orthodontic anchor of the present invention tends to cause only minimal damage to the mandible or maxilla bone or mucous tissues, compared to prior art devices.

DETAILED DESCRIPTION OF PREFERRED EMBODIMENTS

Figure 1:
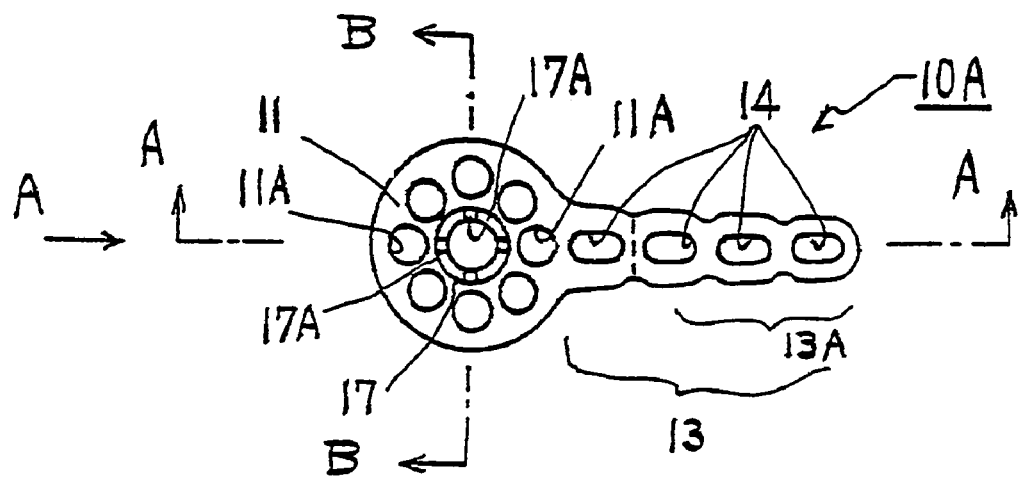
FIG. 1 is a planar view of an orthodontic anchor according to a first embodiment of the present invention.

The present invention is described hereunder in more detail using the accompanying drawings by way of preferred embodiments, but are not intended to limit the present invention.

The orthodontic anchor 10 of the present invention is typically comprised of an anchor plate 11 and an engagement plate 13. The anchor plate 11 is provided with a protrusion 17 and a number of tissue openings 11A around the protrusion 17. The protrusion 17 is inserted into a bore 20 prepared in the mandible or maxilla bone 1 with a boring device 15 to be integrated with the bore 20. In a preferred embodiment, each tissue opening 11A is about 2 mm in diameter.

In a preferred embodiment, the protrusion 17 is a cylinder having a height of 2.8 mm, an outside diameter (D) of 3.5 mm and an inside diameter of 2.5 mm. Typically, the height of the protrusion 17 is "0.8×D" or greater. Preferably, the diameter of the edge of protrusion is a little bit bigger (about p: p=0.2 mm) than the diameter of the bottom, this protrusion is fitted into a bore 20 having a diameter of 3.7 mm in diameter.

In an embodiment, the protrusion 17 is provided with axially extending slits 17A each having an enlarged (round) clearance 17B at its end to provide increased flexibility and stability as well as reliable and easy integration with a bore 20.

The engagement plate 13 is provided with a number of engagement openings 14. In an embodiment, each engagement opening 14 is an eclipse. The engagement opening 14 may be any shape. Alternatively, the engagement openings 14 may be hooking means instead. In an embodiment, such openings 14 and hooking means are provided in combination.

Preferably, the surface of the anchor plate 11 and the surface of the engagement plate 13 are made "smooth" (equal to 0.16 Z or less; ISO) so as not to irritate wearers. Preferably, the engagement plate 13 is tapered (θ2) for ease of embedding operation. Preferably, the edges of the anchor plate 11 and the engagement plate 13 are rounded so as not to irritate wearers. The tissue openings 11A are not limited only to round shapes but may also be polygonal, such as, for example, triangles, squares, pentagons, hexagons, or heptagons and so on.

The engagement plate 13 is made flexible for easy manipulation. The engagement plate 13 partially sticks out into the oral cavity for engagement with teeth biasing means such as wires, spring plates, rubber chains or polymeric chains to provide biasing required for correction of malocclusion. The teeth biasing means are connected in a conventional way with the engagement openings 14 or hooking means. The engagement openings 14 that are not needed or not used may be removed with an appropriate tool. The number of engagement openings 14 may be any number, as long as they are sufficient for biasing the target teeth.

It is preferred that the orthodontic anchor 10 of the present invention is prepared of biologically acceptable, anti-oxidic and flexible material such as a titanium alloy, stainless alloy or cobalt-chrome alloy. In an embodiment, a plate having a thickness "T" of the orthodontic anchor 10 is 0.8 mm. Orthodontic anchors of other sizes can also be used.

The tissue openings 11A are eventually filled in with mucous membrane tissues to partially provide required anchorage after the orthodontic anchor 10 is embedded. There is no limit to the number of the tissue openings 11A in the anchor plate, as long as the tissue openings 11A provide sufficient anchorage.

The ways to appropriately use the orthodontic anchor 10 of the present invention will be readily understood by dentists without specific and detailed instructions.

FIG. 1 shows an orthodontic anchor 10A according to a first embodiment of the present invention. The orthodontic anchor 10A is comprised of an anchor plate 11 and an engagement plate 13. The anchor plate 11 and the engagement plate 13 are integrated into a single piece. The anchor plate 11 is provided with a protrusion 17 and eight tissue openings 11A, and the engagement plate 13 is provided with four engagement openings 14, of which the proximal or base opening 14 or void is used to help provide flexibility to the engagement plate 13 while the distal three openings 14 within the range 13A are exposed into the oral cavity (shown in FIGS. 12 and 13) for use to provide engagement with teeth biasing means (shown in FIGS. 16 and 17).

Figure 2:
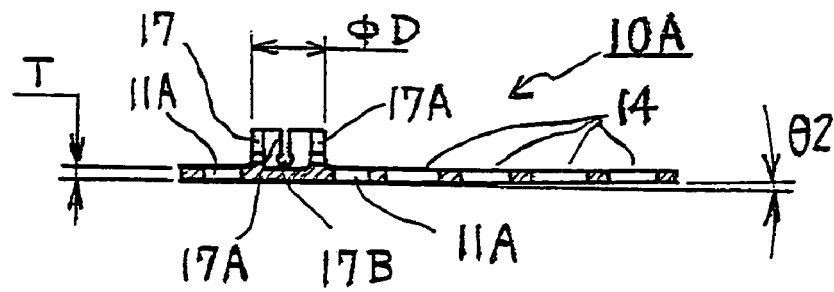
FIG. 2 is a sectional view of the orthodontic anchor of FIG. 1 along line A-A.

FIG. 2 is a sectional view of the orthodontic anchor 10A sectioned along line A-A shown in FIG. 1. The orthodontic anchor 10A is shown having a thickness "T" and taper "θ2". The protrusion 17 is shown having an outside diameter "D".

Figure 3:
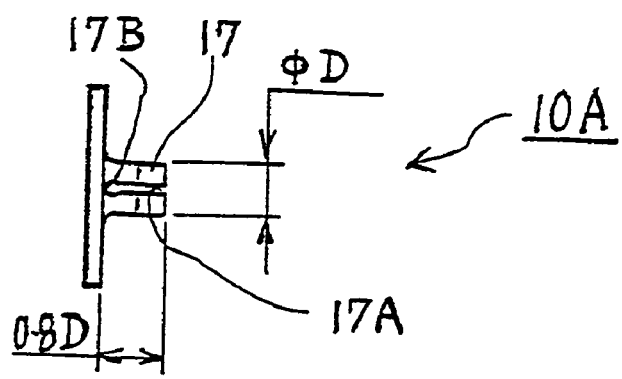
FIG. 3 is a view as seen from side "A" of the orthodontic anchor of FIG. 1.
Figure 12:
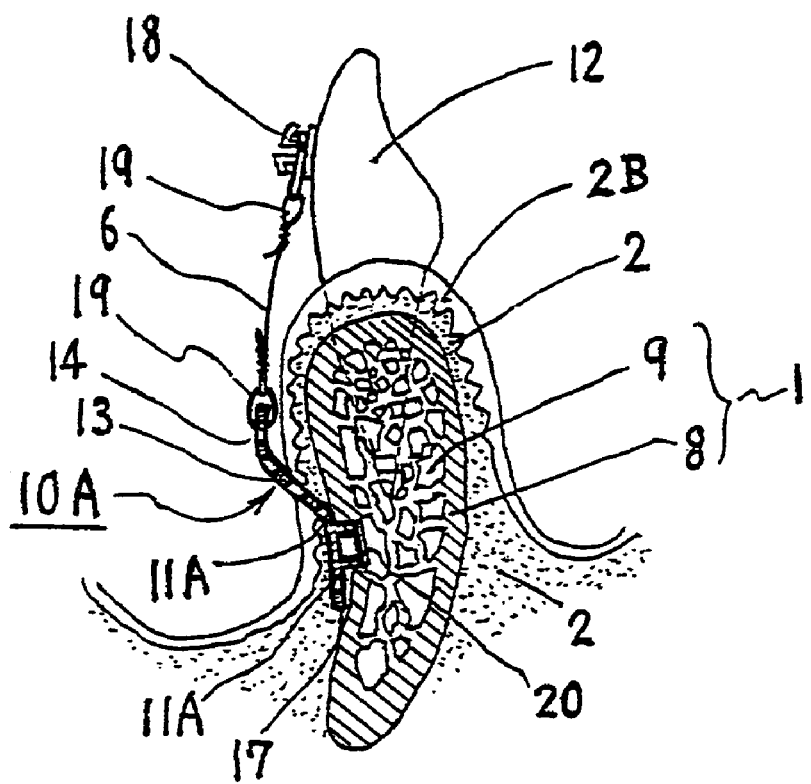
FIG. 12 is a schematic view showing a first state of use of the orthodontic anchor according to the first embodiment of the present invention.

FIG. 3 is a view as seen from side "A" of the orthodontic anchor 10A. The protrusion 17 is shown having a height "0.8 D". The protrusion 17 is provided with slits 17A each having a clearance 17B for provision of easy and reliable integration with a bore 20 as seen in FIG. 12.

Figure 4:
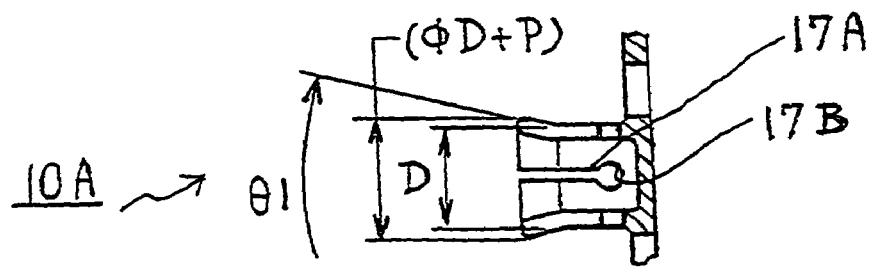
FIG. 4 is a sectional view of the orthodontic anchor of FIG. 1 along line B-B.

FIG. 4 is a sectional view of the orthodontic anchor 10A sectioned along line B-B shown in FIG. 1, showing the size of a bore (20) (not shown here) "D+P" (P=clearance) where the protrusion 17 of the orthodontic anchor 10A fits. The top edge portion of the protrusion 17 is tapered (θ1) to help provide reliable integration with the bore 20.

Figure 5:
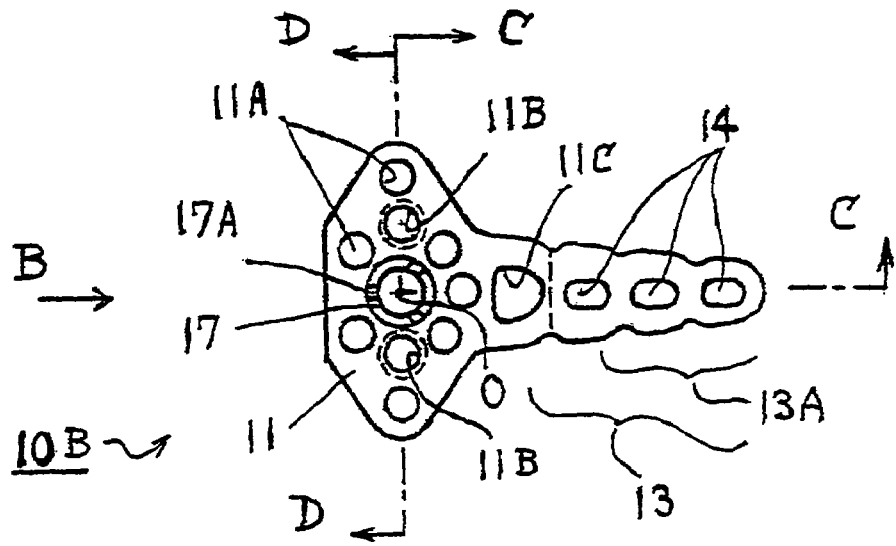
FIG. 5 is a planar view of an orthodontic anchor according to a second embodiment of the present invention.

FIG. 5 shows another orthodontic anchor 10B according to a second embodiment of the present invention. The anchor plate 11 is not circular, but is instead formed as a deformed eclipse. The anchor plate 11 is provided with a protrusion 17 whose wall is separated into three axially extending portions with axially extending slits 17A each having a clearance 17B. The anchor plate 11 is also provided with seven tissue openings 11A. It is possible to have more tissue openings 11A because the anchor plate 11 is large enough to accommodate more. The anchor plate 11 is additionally provided with two tapered edge holes, or screw openings 11B, to accept screws. A screw (not shown in the figure) is inserted into each screw opening 11B to be screwed into the mandible or maxilla bone (not shown) to provide additional anchorage. As such, an according to FIG. 5, orthodontic anchor is capable of providing greater anchorage than the orthodontic anchor shown in FIG. 1.

The engagement plate 13 of the orthodontic anchor 10B is wider than the corresponding part of the orthodontic anchor 10A and thus can bear a greater biasing force. The engagement plate 13 is provided with three engagement openings 14 within the exposing range 13A and a void or a lightening hole 11C which helps provide improved flexibility or maneuverability to the engagement plate 11.

Figure 6:
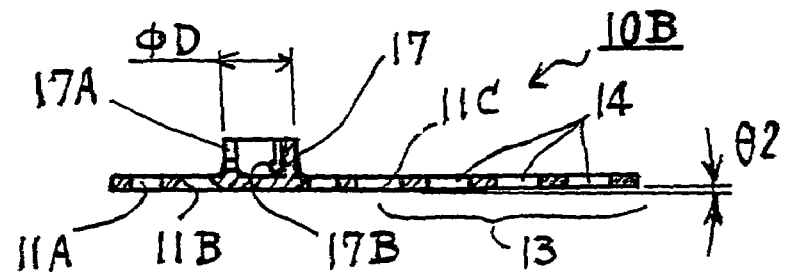
FIG. 6 is a sectional view of the orthodontic anchor of FIG. 5 along line C-O-C.

FIG. 6 shows a sectional view of the orthodontic anchor 10B sectioned along line C-O-C shown in FIG. 5.

Figure 7:
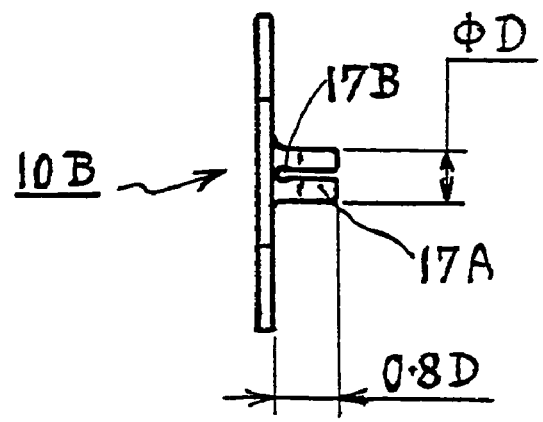
FIG. 7 is a view as seen from side "B" of the orthodontic anchor of FIG. 5.

FIG. 7 is a view as seen from side "B" of the orthodontic anchor 10B of FIG. 5.

Figure 8:
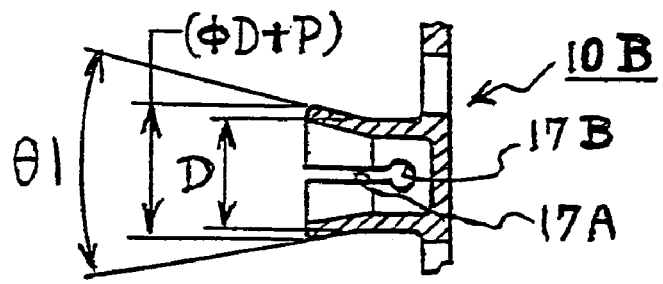
FIG. 8 is a sectional view of the orthodontic anchor of FIG. 5 along line D-D.

FIG. 8 shows a sectional view of the orthodontic anchor 10B sectioned along line D-D shown in FIG. 5.

Figure 9:
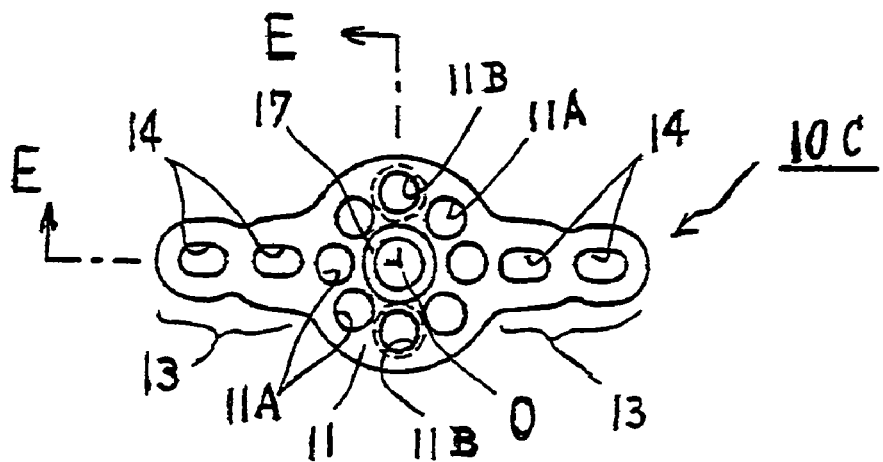
FIG. 9 is a planar view of an orthodontic anchor according to a third embodiment of the present invention.
Figure 16:
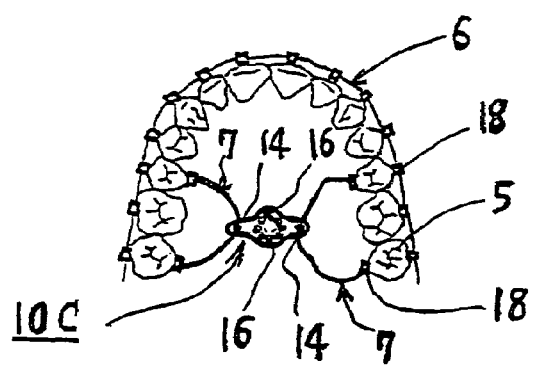
FIG. 16 is a schematic view showing a first state of use of the orthodontic anchor according to the third embodiment of the present invention.

FIG. 9 shows another orthodontic anchor 10C according to a third embodiment of the present invention. This orthodontic anchor 10C has two oppositely positioned engagement plates 13, which are secured to the upper jaw bone (not shown). This orthodontic anchor 10C is suitable for use as shown in FIG. 16.

Figure 10:
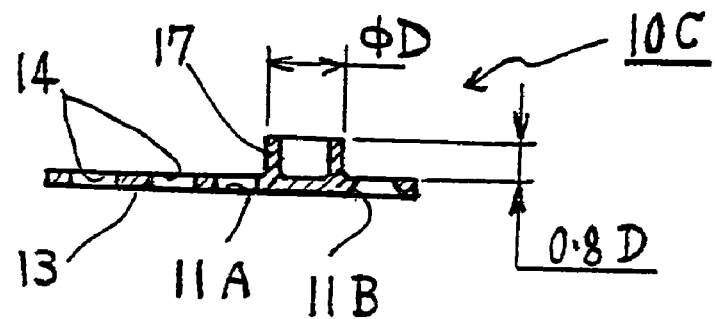
FIG. 10 is a sectional view of the orthodontic anchor of FIG. 9 along line E-O-E.

FIG. 10 is a sectional view of the orthodontic anchor 10C sectioned along line E-O-E shown in FIG. 9.

Figure 11:
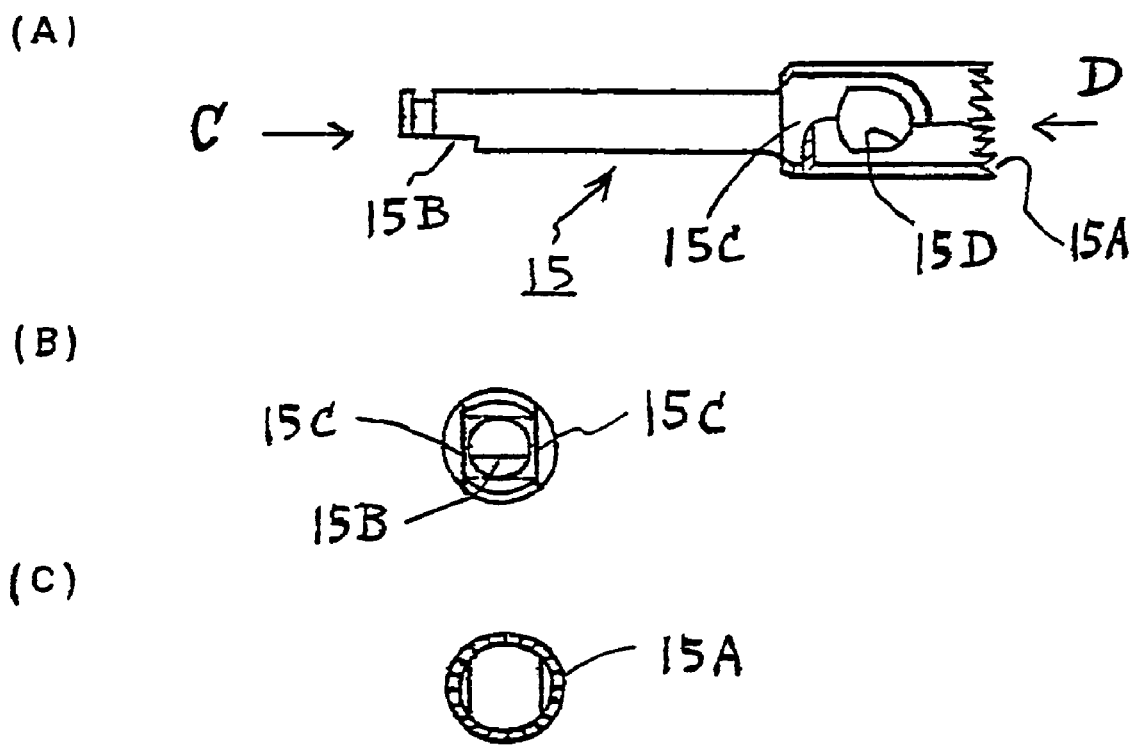
FIG. 11(A) is a planar view of a boring device.
FIG. 11(B) is a view as seen from side "C" of the boring device of FIG. 11(A)
FIG. 11(C) is a view as seen from side "D" of the boring device of FIG. 11(A)

FIG. 11(A) shows an example boring device 15 or hole saw comprised of a cutter end 15A, base portion 15B, cylinder 15C and holes 15D. The boring device 15 is connected to a motor means and used like an end mill to prepare a bore 20 in the mandible or maxilla bone 1. FIG. 11(B) is a view as seen from side "C" of the boring device 15 shown in FIG. 11(A). FIG. 11(C) is a view as seen from side "D" of the boring device 15 shown in FIG. 11(A).

In the following are described processes to use the orthodontic anchor 10.

FIG. 12 shows in a schematic view a first state of use of the orthodontic anchor 10A. A bore 20 is prepared in the mandible or maxilla bone 1 (cortical bone 8 and spongy bone 9) with a boring device 15. The orthodontic anchor 10A is secured to the mandible or maxilla bone 1 with the protrusion 17 inserted into the bore 20. The anchor plate 11 is placed between the mandible or maxilla bone 1 and the mucous membrane 2 (penetrated membrane portion 2A; epithelium 2B). The engagement protrusion 13 is partially exposed, which is connected to a wire 6 with a polymeric chain 19. The wire 6 is secured to a tooth 12 with a ligament device such as a polymeric chain or rubber 19 to achieve orthodontic force.

Figure 13:
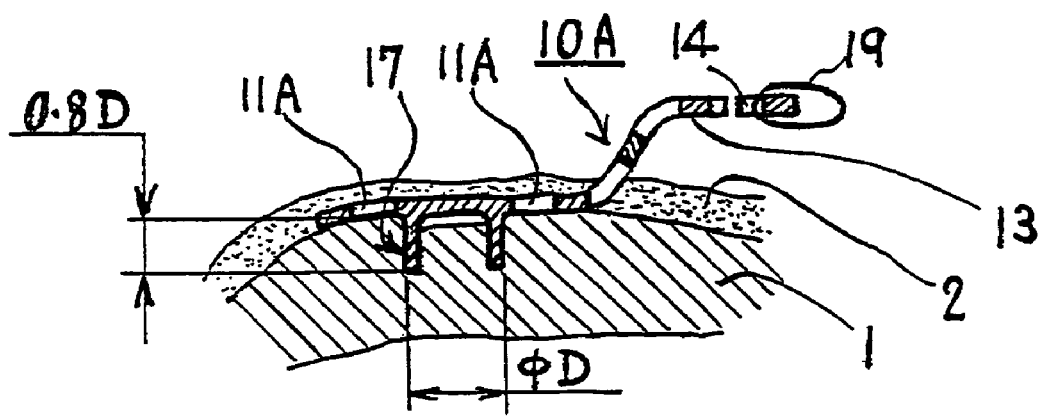
FIG. 13 is a schematic view showing a second state of use of the orthodontic anchor according to the first embodiment of the present invention.

FIG. 13 schematically shows a second state of use of the orthodontic anchor 10A, showing that the engagement plate 13 is bent.

Figure 14:
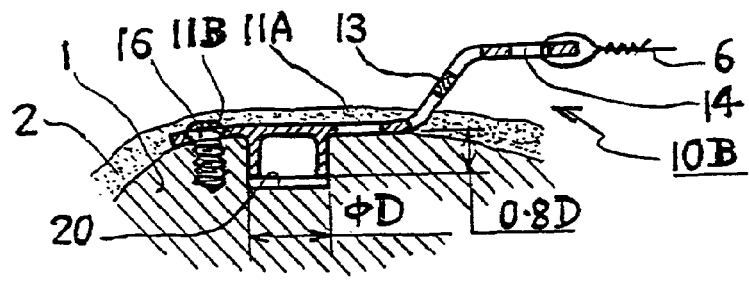
FIG. 14 is a schematic view showing a first state of use of the orthodontic anchor according to the second embodiment of the present invention.

FIG. 14 is a schematic view showing a first state of use of the orthodontic anchor 10B. Screws 16 are used to assist in providing additional anchorage.

Figure 15:
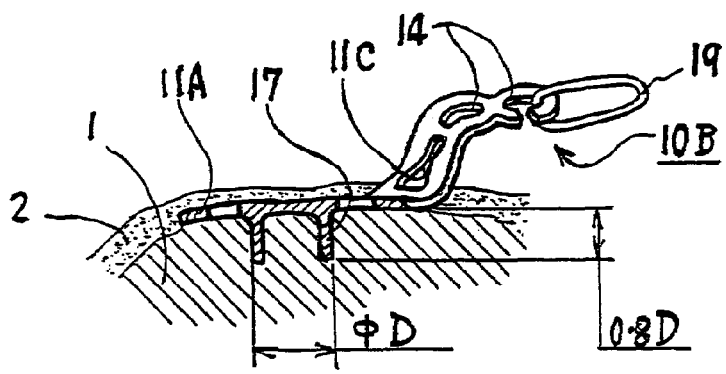
FIG. 15 is a schematic view showing a second state of use of the orthodontic anchor according to the second embodiment of the present invention.

FIG. 15 schematically shows a second state of use of the orthodontic anchor 10B, where the engagement plate 13 is twisted helped by the void or the lightening hole 11C. By means of the change of geometric moment of torsion by means of lightening hole, it becomes easier to bend the engagement plate 13.

FIG. 16 schematically shows a first state of use of the orthodontic anchor 10C. The orthodontic anchor 10C is secured to the upper jaw bone (not shown). Spring plates 7 extend from the orthodontic anchor 10C to teeth 5, respectively.

Figure 17:
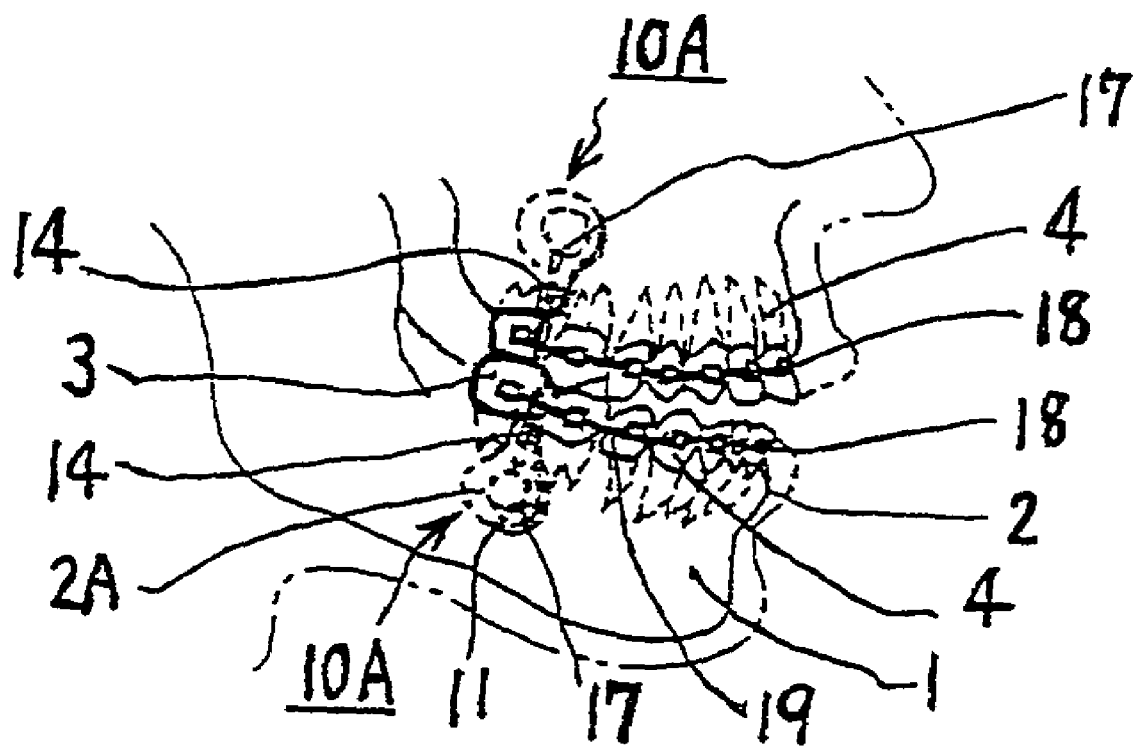
FIG. 17 is a schematic view showing another state of use of the orthodontic anchor according to the first embodiment of the present invention.

FIG. 17 schematically shows another state of use of the orthodontic anchor 10A to move premolar 4 with molar 3 as a starting point. Buttons or brackets 18 are used to secure the polymeric or rubber chain 19 to premolar 4 and molar 3.

This invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An orthodontic anchor for securing to a bone underlying the mucous membrane, the bone having a bore, the orthodontic anchor comprising:
   an anchor plate having at least one tissue opening and a protrusion that can be inserted and fixed to the bore in the bone; and
   an engagement plate extending from the anchor plate, the engagement plate having at least two engagement openings, and wherein the protrusion has at least one axially extending slit having an open end and a closed end, the slit having an enlarged clearance at the closed end.

2. The orthodontic anchor of claim 1, wherein the engagement openings each have an elliptical shape.

3. The orthodontic anchor of claim 1, wherein at least one of the tissue openings has a polygonal shape.

4. The orthodontic anchor of claim 1, wherein at least one of the engagement openings is an open slot defining a hook.

5. The orthodontic anchor of claim 1, wherein a portion of the engagement plate can be detached from the orthodontic anchor, thereby removing at least one of the engagement openings.

6. The orthodontic anchor of claim 1, wherein the engagement openings are positioned to secure a spring or rubber wire to obtain orthodontic force.

7. The orthodontic anchor of claim 1, wherein the anchor plate further comprises at least one tapered edge hole to accept a fastener.

8. The orthodontic anchor of claim 1, wherein the engagement plate further comprises a void to provide improved maneuverability to the engagement plate.

* * * * *